United States Patent [19]

O'Sullivan

[11] Patent Number: 5,168,590
[45] Date of Patent: Dec. 8, 1992

[54] THERAPEUTIC PILLOW COVER HAVING COMPARTMENTS FOR RECEIVING HOT/COLD PACKS AND/OR PILLOW INSERT SUPPORTS

[76] Inventor: Dennis O'Sullivan, 330 Golden Gate, Belvedere, Calif. 94920

[21] Appl. No.: 590,659

[22] Filed: Sep. 28, 1990

[51] Int. Cl.⁵ .............................................. A47G 9/02
[52] U.S. Cl. ............................................ 5/490; 5/485; 5/640; 5/639; 5/636; 5/421
[58] Field of Search .................. 5/485, 490, 434, 436, 5/437, 442, 446, 465, 421, 636-645

[56] References Cited

U.S. PATENT DOCUMENTS

| D. 282,427 | 2/1986 | O'Sullivan | D6/601 |
|---|---|---|---|
| 3,243,828 | 4/1966 | McCarty | 5/437 |
| 3,638,251 | 2/1972 | Weiss | 5/334 |
| 3,849,810 | 11/1974 | Degen | 5/341 |
| 4,309,784 | 1/1982 | Cohen | 5/442 |
| 4,688,286 | 8/1987 | Milker | 5/490 |
| 4,754,513 | 7/1988 | Rinz | 5/490 |
| 4,783,866 | 11/1988 | Simmons | 5/442 |
| 4,853,994 | 8/1989 | Ekstein | 5/437 |
| 4,945,589 | 8/1990 | Carey | 5/442 |
| 4,949,411 | 8/1990 | Tesch | 5/442 |

FOREIGN PATENT DOCUMENTS

| 3138463 | 9/1981 | Fed. Rep. of Germany . | |
|---|---|---|---|
| 1127948 | 12/1956 | France | 5/337 |
| 1837 | 6/1837 | United Kingdom | 5/490 |
| 16809 | 6/1908 | United Kingdom . | |
| 26072 | 12/1909 | United Kingdom . | |

Primary Examiner—Renee S. Luebke
Assistant Examiner—F. Saether
Attorney, Agent, or Firm—Limbach & Limbach

[57] ABSTRACT

A therapeutic pillow covering (100) for covering either a prefabricated conventional or therapeutic pillow (200) having a central depression region (210), or for encasing pillow fill having a plurality of compartments (12, 14, 16) for holding a prefabricated pillow insert (22, 28) or a hot or cold pack (26). The compartments (12, 14, 16) each have an opening (13, 15, 17) for insertion and removable of the inserts (22, 26, 28). The pillow covering (100) has a center compartment (14) located about in the center of the pillow cover; two oppositely disposed side wing compartments (12) located on opposite ends of the pillow cover (100); and two oppositely disposed hot/-cold pack compartments (16) parallel to the center compartment (11) and on opposite sides of the center compartment (14). The compartments (12, 14, 16) may be affixed either to the interior of the cover (100) or to the exterior of the cover (100). The cover (100) may have boxed off corners (20). The opening (13, 15, 17) may be closed using a fastener such as Velcro, snaps, or a zipper.

38 Claims, 3 Drawing Sheets

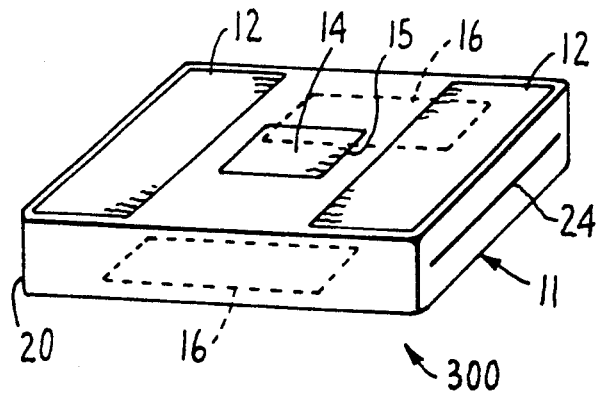
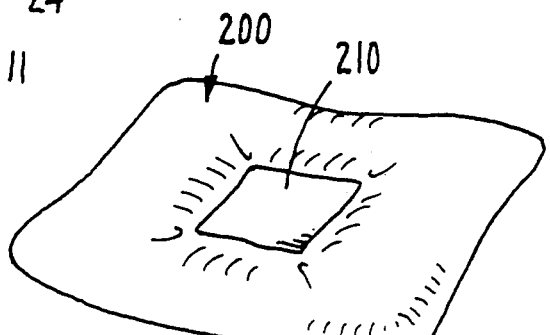
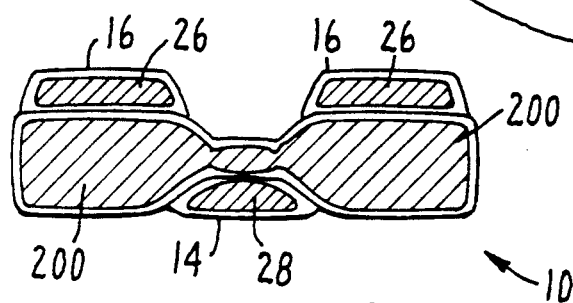
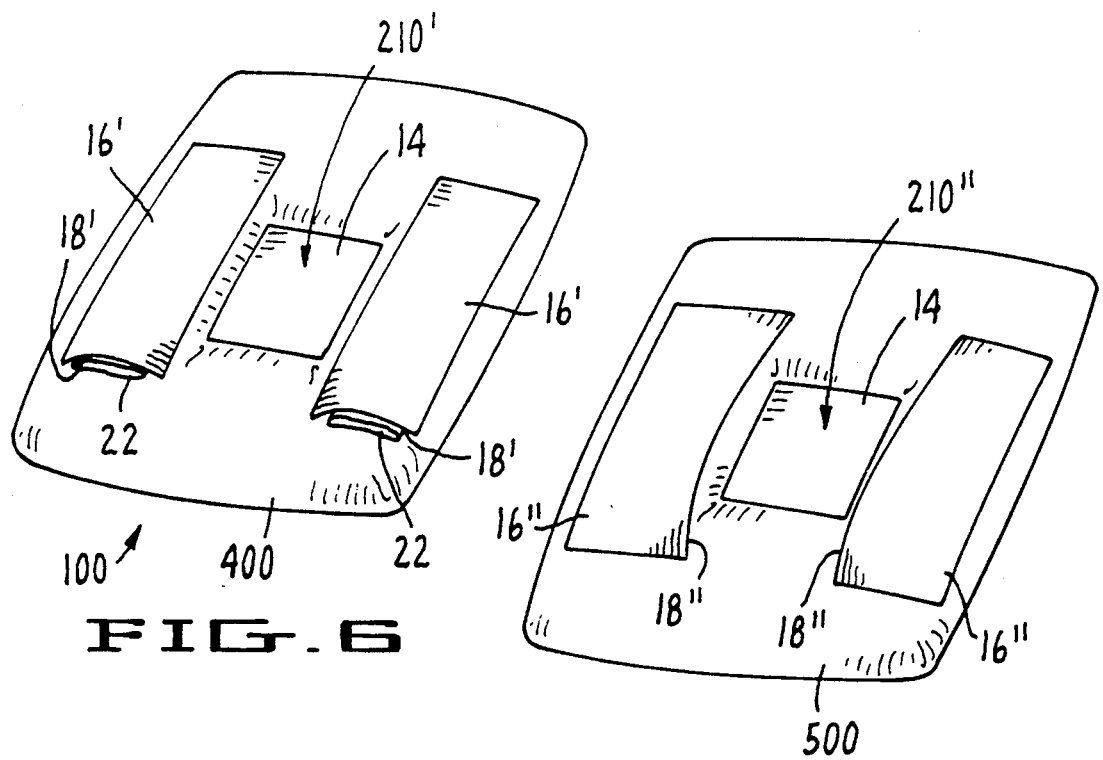
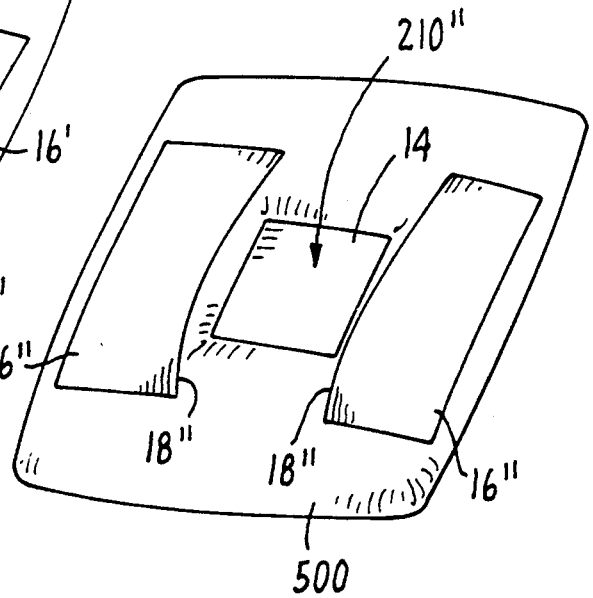

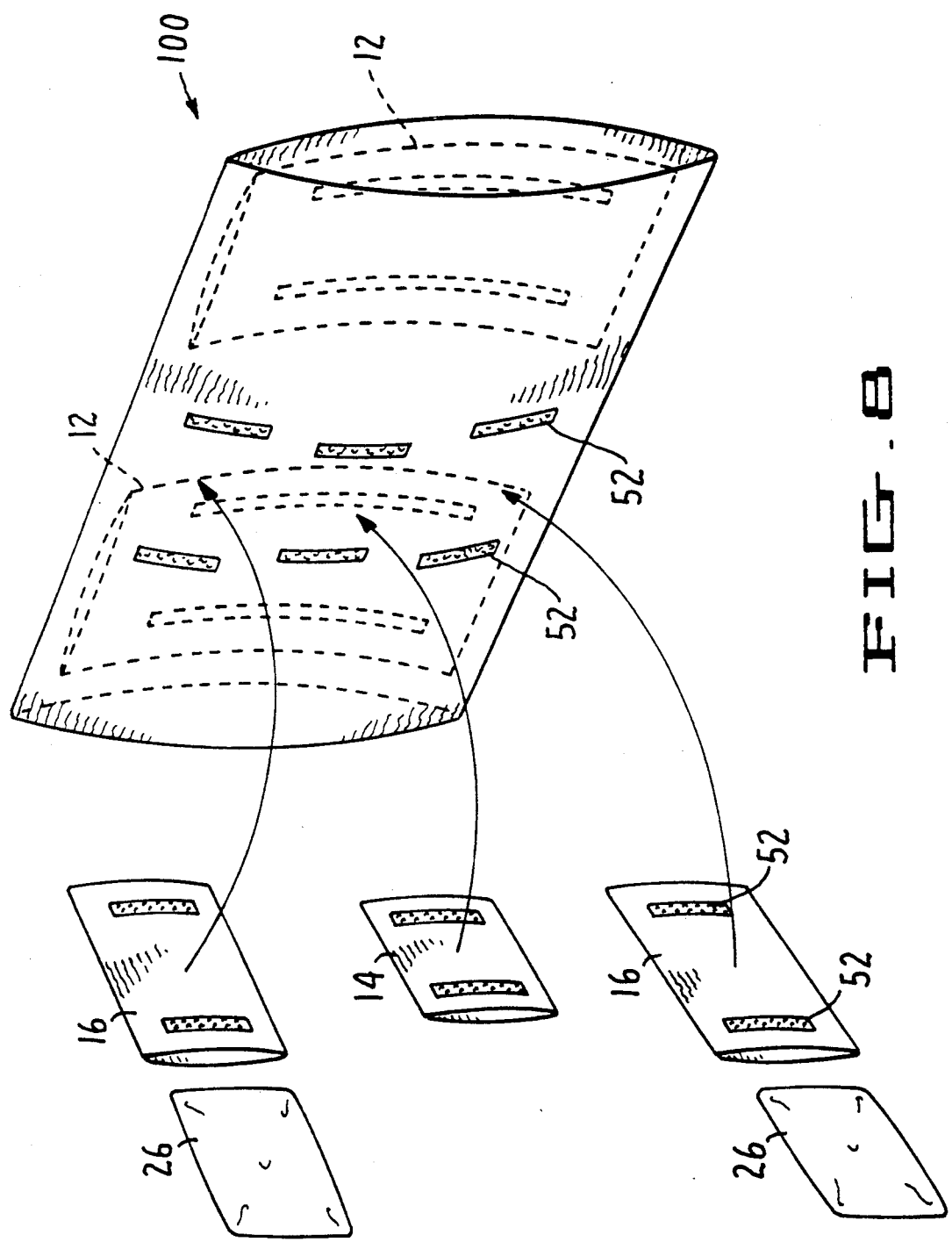

THERAPEUTIC PILLOW COVER HAVING COMPARTMENTS FOR RECEIVING HOT/COLD PACKS AND/OR PILLOW INSERT SUPPORTS

TECHNICAL FIELD

The present invention broadly relates to pillow coverings and, more particularly, to a pillow covering having a plurality of compartments for holding pillow inserts or hot/cold packs. The therapeutic pillow covering may be used as a pillow case or to encase filling for a pillow.

BACKGROUND ART

Orthopedic pillows and pillow cases have been developed to support the head and neck. U.S. Pat. No. 4,754,513 to Rinz, for example, discloses a pillow case with a single compartment, extending the length of one of the long sides of a standard rectangular pillow, for holding an elastomeric insert. The insert is designed to support a person's neck. However, the pillow case does not provide support for the side of the person's head and does not provide a way for the user to adjust the thickness of the center region of the pillow, the sides of the pillow, the top of the pillow, or the bottom of the pillow.

Orthopedic pillows having several sections have also been developed. However, these pillows and pillow covers tend to be bulky and cumbersome. For example, U.S. Pat. No. 3,849,810 to Degen shows a pillow and pillow case made up of three interconnecting sections of equal size. Each section is separated by a vertical cut which extends part-way down the pillow and pillow case. The central section is about half as thick as the other two sections. By adding an additional panel capable of being rolled up, to the central section of the pillow case, the pillow may be modified to include a neck roll. The disadvantage with the Degen pillow is that forming the neck roll section is cumbersome. The user has to roll up the panel and place it in a compartment in the pillow case. Another disadvantage of the Degen pillow is that the rolled up panel may come unrolled while it is being used.

Some of orthopedic pillows have two parallel neck roll compartments. German patent DE 3138463 A1 to Jackle for instance shows a pillow case having two compartments for holding a support pillow which extends for the entire length of the pillow case. While the dual parallel compartments provide a place to hold head and neck support pillows a user does not have the ability to adjust the thickness of other parts of the pillow (e.g., the depth of the center of the pillow where the user places his head or the thickness of the short sides of the pillow).

SUMMARY OF THE INVENTION

The present invention is directed to a pillow cover for a pillow. The pillow cover may cover a prefabricated conventional or therapeutic pillow or it may serve as the shell to encase pillow fill. The pillow cover is comprised of a front panel and a back panel which are attached together on at least two sides.

The front panel has a first front end region and a second front end region and the back panel a first back end region and a second back end region. The back panel is opposed to the front panel such that the second front end region is across from the first front end region and the second back end region is across from the first back end region. The front and back panels may be attached together in a manner wherein a corner is formed thereby giving the pillow cover depth.

The pillow cover has a first side pocket attached to one of the first end regions and a second side pocket attached to one of the second end regions. Both the first and the second side pocket have an opening for inserting/removing an object. The pillow cover also has a center pocket which is attached to the front panel in about the center of the front panel. The center pocket also has an opening so that a center pillow insert may be inserted/removed.

The pockets may be attached to either the exterior side or to the interior side of either the front or the back panels. The pockets may either be permanently attached or removably attached to the panels.

The pillow cover may further include third and fourth side pockets. The third side pocket is attached to one of the panels in a third end region, where the third end region is perpendicular to the first end region; and the fourth side pocket is attached to one of the panels in a fourth end region, where the fourth end region is across from the third end region.

It is therefore a primary object of the present invention to provide a pillow cover having a plurality of compartments to permit a person to change the elevation and curvature of separate regions of a pillow.

Another object of the present invention is to provide a pillow cover having a center compartment for insertion of a pillow to adjust the thickness of the center of a pillow.

An additional object of the present invention is to provide a pillow cover having compartments for holding hot/cold packs.

A further object of the invention is to provide a pillow cover having corners to give depth to the cover such that a pillow housed therein substantially maintains its shape.

These, and further objects and advantages of the present invention will be made clear or will become apparent during the course of the following description of the preferred embodiment of the present invention.

BRIEF DESCRIPTION OF THE DRAWINGS

In the accompanying drawings:

FIG. 3 is an alternate back perspective view of the pillow cover of the present invention having boxed corners;

FIG. 4 is a sectional view taken along line A—A of FIG. 2;

FIG. 5 is a top, front perspective view of a conventional therapeutic pillow having a central depression region;

FIG. 6 is a back perspective view, similar to FIG. 2, of an alternate pillow cover encasing pillow fill; and FIG. 7 is a back perspective view, similar to FIG. 6 of yet another alternate pillow cover encasing pillow fill.

FIG. 8 is a perspective view of the pillow cover illustrating the compartments fastened on the interior of the pillow cover and a removable compartment.

DETAILED DESCRIPTION OF THE PREFERRED

Figure 1:
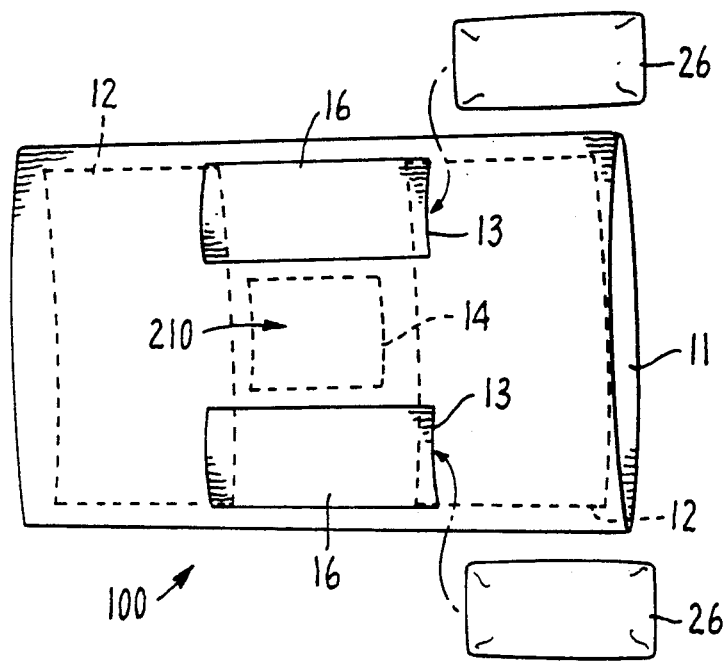
FIG. 1 is a front perspective view of the pillow cover of present invention.
Figure 2:
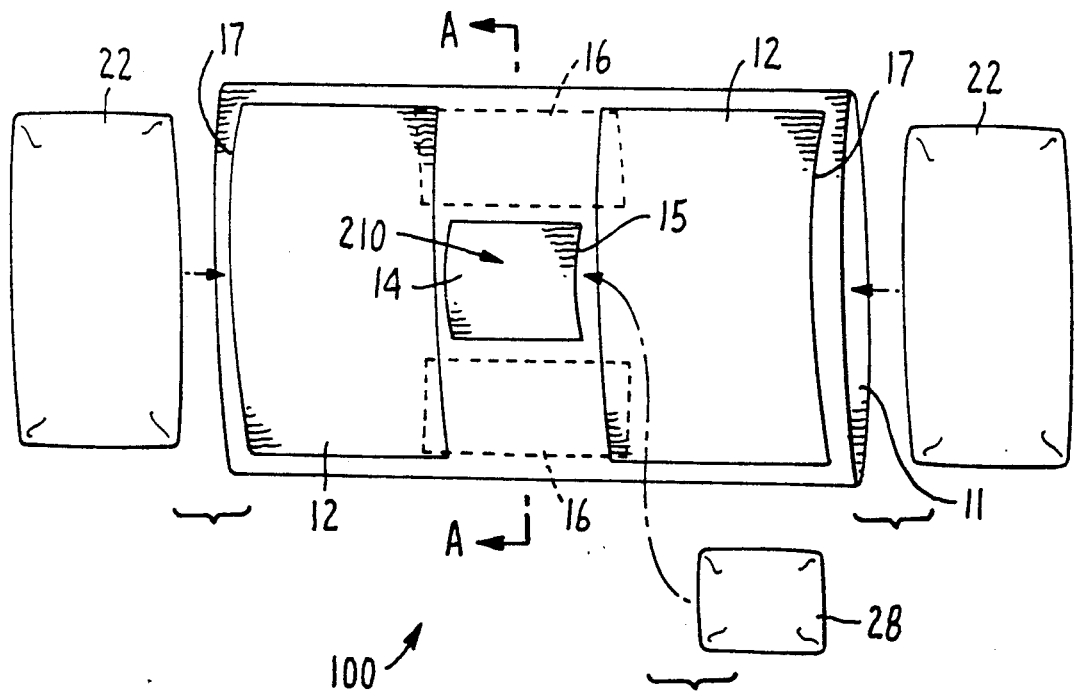
FIG. 2 is a back perspective view of the pillow cover shown in FIG. 1.

Referring to FIGS. 1, 2 and 5 a therapeutic pillow cover 100, also referred to as a cover element, for covering either a prefabricated pillow or for serving as a shell for encasing pillow fill to form a pillow, is illustrated. While the pillow cover 100 may be used to cover a conventional pillow, it is preferably used to cover a health pillow 200 as shown in FIG. 5 and in U.S. Pat. No. Des. 282,427 and having a central, padded depression region or center pocket 210. The pillow cover 100 has an open end 11 to permit the pillow 200 to be inserted and removed from the cover 100. As illustrated, the pillow cover 100 is rectangular, however, it may be any shape: round, square, oval, triangular or trapezoidal.

In the preferred embodiment, the pillow cover 100 has five compartments: a center compartment 14, two oppositely disposed hot/cold pack compartments 16, and two oppositely disposed side wing compartments 12. Compartments 12, 14, 16 permit a person to change the elevation and curvature of separate regions of a pillow to derive maximum support and comfort.

The center compartment 14 is attached on a first back side of the pillow cover 100 in about the center of the cover 100. The center compartment is stitched to the cover 100. When a person lies on the pillow cover 100, his head rests approximately in the central depression region 210 and on the center compartment 14. The center insert 28 permits the user to have the option to adjust the thickness of the central depression region 210 (or in general, the depth of the central region of a pillow) to achieve a more desirable comfortable level.

The center compartment 14 is about the same size and shape as, or larger than the central depression region 210 of the pillow 200 that is to be covered.

In the preferred embodiment, the center compartment 14 is rectilinear-shaped. However, the size and shape of the center compartment 14 may be varied to accommodate central depression regions 210 of different sizes and shapes. (e.g., rectangular regions, trapezoidal regions, squares, ovals, circles, etc). As illustrated, two sides of the insert 28 are parallel to the two long sides of the pillow cover 100.

The pillow cover 100 also has a pair of front side hot/cold pack compartments 16, one being located in the top region and the other being located in the bottom region. Each of the hot/cold pack compartments 16 is centered along the long side of the pillow cover 100 opposite from one another. The hot/cold pack compartments 16 are rectangular shaped. Their long sides are attached to the pillow cover 100 parallel to the long side of the cover. The hot/cold pack compartments 16 are preferably about one half as long as the long side of the pillow cover 100. Short side of the compartment 16 generally extends from about the exterior edge of the pillow cover 100 to about the edge of the center compartment 14.

The compartments 16 have an opening 13 from which a hot/cold pack 26 or a pillow insert may be inserted or removed. At least two of the edges of the compartment 16 are stitched to the cover 100. In the preferred embodiment, one of the short ends 13 of the compartment 16 is left open to permit the insertion and removal of the hot/cold pack 26. The open end 13 may be fastened closed via conventional fasteners such as Velcro, snaps, zipper, buttons, etc.

In the illustrated embodiment the hot/cold pack compartments 16 are attached on a second front side of the pillow cover 100 as shown in FIG. 1 and the perimeter of the hot/cold pack compartments 16 are shown in phantom in FIG. 2. In alternate embodiments, the center compartment 14 and hot/cold pack compartments 16 may be attached on the same side of the pillow cover 100.

The pillow covering 100 also has a pair of side wing compartments 12; one side wing compartment 12 is attached in the left region while the other side wing compartment 12 is attached in the right region. The compartments 12 are rectangular shaped and are attached to the cover 100 with their long sides parallel to the short sides of the pillow cover 100. The side wing compartments 12 may be attached on the same side of the pillow cover 100 or on opposite sides. As illustrated, the pair of side wing compartments 12 are attached on the same back side of the pillow cover 100 across form one another and also attached on the same side as the center compartment 14. Hence, the center compartment is 14 in between the side wing compartments 12.

The length of the short sides of the compartment 12 is about equal to one third of the length of the pillow cover 100.

The side wing compartments 12 are stitched to pillow cover 100 on three sides and open on one side 17 to permit therefrom a pillow insert to be inserted and removed. The pillow insert 22 helps support a person's face when he is laying on his side. The open ends of the compartments may be fastened together using a strip of Velcro.

In the preferred embodiment, where the pillow cover 100 is used as a pillow case to cover a prefabricated pillow, the compartments 12, 14, 16 are permanently affixed to the cover 100 on the interior of the pillow cover 100. FIG. 8 illustrates the side wing compartments 12 fastened to interior wall 50 of pillow cover 100. However, the compartments 12, 14, 16 may be sewn on the cover's exterior.

Referring to FIG. 3, pillow cover 300 having boxed corners 20 is illustrated. The pillow cover 300 may be used as a pillow case to cover either a conventional pillow, or more preferably, the health pillow 200. The boxed off corners 20 give the pillow cover more depth so that the pillow that is covered is not compressed when it is housed inside the cover 300. Hence the boxed off corners 20 protect the pillow from having its shape substantially altered.

The pillow cover 300 also has an open end 11 where the pillow to be encased is inserted/removed. The opening may also be closed by Velcro or other fasteners such as a zipper, snaps, buttons, etc.

Alternate embodiments of the pillow cover 100 may have the compartments 12, 14, 16 removably attached to the pillow cover 100 via snaps, fasteners, Velcro or the like, either on the interior or the exterior of the pillow cover 100. FIG. 8 illustrates one method of removably attaching the compartments 16 to the pillow cover 100 by way of Velcro strips 52. Velcro strips 52 are mounted on one side of the compartment 16, as well as the pillow cover 100 where compartment 16 is to be attached. Compartment 16 is easily attached to the pillow cover 100 by pressing it against same. The Velcro strips 52 may be of any shape, size and quantity suitable for fastening the compartments to the pillow cover, e.g., square, circular, triangular, etc.

When the pillow cover 100 is used as the shell, to contain pillow fill making up a sleeping pillow, it is preferable for the compartments 12, 14, 16 to be located on the exterior of the pillow cover 100.

Referring to FIG. 4, a cross sectional view of the pillow cover 100, 300 showing the pillow 200 and the inserts 28, 26 is illustrated. The center pillow insert 28 is housed in the center compartment 14 and is in alignment with the central depression region 210 of the health pillow 200. The hot/cold pack compartments 16 contain the hot packs 26.

FIGS. 6 and 7 shows two alternate pillow covers 400, 500 respectively used as the shell for encasing pillow fill, thereby forming a health pillow 400, 500. As previously discussed, when the cover 100 is used to encase pillow fill, the compartments 12, 14, 16, are preferably attached to the exterior of the cover 100. The pillows 400, 500 have a center pocket or central depression region 210' and 210" respectively.

The center compartment 14 may be attached to the pillow cover over the central depression region 210. In the preferred embodiment, the compartment 14 is stitched to the central depression region. If the center compartment 14 is attached to the pillow cover, it may have an open side 15 to permit the central pillow insert 28 to be inserted/removed. Alternatively, the center pocket 14 may be formed by stitching the front and back panels together.

Referring to FIG. 6, the hot/cold pack compartments 16' are stitched to the cover 400 on at least two sides and has one of its short sides 18' open. Referring to FIG. 7, which is similar to FIG. 6, the hot/cold pack compartments 16" are stitched to the cover 500 on three sides and has one of its long sides 18" open.

The compartments 12, 14, 16 may include a pleat so that the compartment may be enlarged. In the preferred embodiments, the pillow cover 100, 400, 500 and the compartment attachments 14, 16, 18 are made out of the same material. However, the cover 100, 400, 500 and the compartments 12, 14, 16 may be fabricated out of different materials. For example, the compartments may be made out of an elastic material.

The health pillow 200 or a conventional pillow may be enhanced by the pillow user having the option of attaching any one, or a combination of, the compartments 14, 16, 18 directly onto the pillow 200 using any type of removable fastener, such as Velcro strips 52 illustrated in FIG. 8. To make the enhanced pillow more comfortable to sleep on, the enhanced pillow can be covered with a standard pillow case.

Having thus described the invention, it is recognized that those skilled in the art may make various modifications or additions to the preferred embodiment chosen to illustrate the invention without departing from the spirit and scope of the present contribution to the art. Accordingly, it is to be understood that the protection sought and to be afforded hereby should be deemed to extend to the subject matter claimed and all equivalents thereof within the scope of the invention.

What is claimed is:

1. A pillow cover for a pillow having a front panel having a first front end region and a second front end region and a back panel having a first back end region and a second back end region, the front panel being opposed to the back panel and being attached thereto on at least two sides, and wherein the second front end region being across from the first front end region and the second back end region being across from the first back end region, the pillow cover comprising:

a first side pocket attached to one of the first end regions, wherein the first side pocket having a first opening for inserting/removing a first object;

a second side pocket attached to one of the second end regions, wherein the second side pocket having a second opening for inserting/removing a second object;

a center pocket in about the center of the pillow cover;

wherein the front panel having an interior side and an exterior side, and the back panel having an interior side and an exterior side;

wherein the center pocket being attached to the exterior side of the front panel, the first side pocket being attached to one of the exterior sides, and the second side pocket being attached to one of the exterior sides; and wherein the center pocket is removable, the first side pocket is removable, and the second side pocket is removable.

2. A pillow covering having two substantially rectangular cover panels having opposed long sides and short sides, the two cover panels being joinable along at least three sides to form the pillow covering for a pillow having a rectilinear depression substantially in the center of the pillow, wherein each cover panel having a right side region, a left side region a top region, a bottom region, and a center region corresponding to about the location of the rectilinear depression, the pillow covering comprising:

a central panel attached to one of the cover panels substantially in the center region, wherein the central panel having an opening for inserting/removing a center insert to be housed therein;

two substantially rectangular vertical panels each vertical panel having two opposed long sides and two short sides, wherein the length of the long sides of the vertical panel being substantially the length of the short side of the cover panels, wherein one of the vertical panels being attached in one of the right side regions and the other one of the vertical panels being attached in one of the left side regions, wherein the vertical panels being attached with its long sides being substantially parallel to the short side of the cover panel, and wherein each of the vertical panels having an opening for inserting/removing a vertical insert to be housed therein; and two substantially rectangular horizontal panels each horizontal panel having two long sides and two short sides, wherein one of the horizontal panels being attached in one of the top regions and the other one of the horizontal panels being attached in one of the bottom regions, the horizontal panels being attached with its long sides substantially parallel to the long sides of the cover panel, and wherein each of the horizontal panels having an opening for inserting/removing a horizontal insert to be housed therein.

3. The pillow covering of claim 2, wherein the center panel and the vertical panels are attached to the same one of the cover panels.

4. The pillow covering of claim 3, wherein each of the cover panels has an interior face and an exterior face, and wherein:

the center panel and the vertical panels being attached on the interior of the one cover panel.

5. The pillow covering of claim 3, wherein the horizontal panels are attached to the other one of the cover panels.

6. The pillow covering of claim 3, wherein each of the cover panels has an interior face and an exterior face, and wherein:
the horizontal panel being attached to the interior face of the other one of the cover panels.

7. The pillow covering of claim 2, wherein:
the length of the short side of the vertical panels being at least one quarter the length of the long side of the cover panel.

8. The pillow covering of claim 7, wherein the length of the short side of the vertical panel being about one third the length of the long side of the cover panel.

9. The pillow covering of claim 2, wherein:
the length of the long side of the horizontal panels being at least about equal to one third the length of the long side of the cover panel.

10. The pillow covering of claim 9, wherein:
the long side of the horizontal panels being about equal to one half the length of the long side of the cover panel.

11. The pillow covering of claim 2, further including:
corner means for forming a corner where one of the cover panel short sides and an adjacent one of the cover panel long sides is joined with the opposed one of the cover panel short sides and the opposed one of the cover panel long sides.

12. The pillow covering of claim 11, wherein the pillow cover includes at least two corners.

13. The pillow covering of claim 2, further including:
pillow fill positioned in between the cover panels, wherein the cover panels being joined together along at least three of the opposed sides.

14. A pillow covering having two substantially rectangular cover panels having opposed long sides and short sides, the two cover panels being joinable along at least three sides to form the pillow covering for a pillow having a rectilinear depression substantially in the center of the pillow, wherein each cover panel having a right side region, a left side region, a top region, a bottom region, and a center region corresponding to about the location of the rectilinear depression, the pillow cover comprising:
a central panel attached to one of the cover panels substantially in the center region, wherein the central panel having an opening for inserting/removing a center insert to be housed therein; and
two substantially rectangular horizontal panels each having two long sides and two short sides, wherein one of the horizontal panels being attached in one of the top regions and the other one of the horizontal panels being attached in one of the bottom regions, the horizontal panels being attached with its long sides substantially parallel to the long sides of the cover panel, and wherein each of the horizontal panels having an opening for inserting/removing a horizontal insert to be housed therein.

15. The pillow covering of claim 14, wherein each of the cover panels has an interior face and an exterior face, and wherein:
the central panel being attached on the exterior face of one cover panel and the horizontal panels being attached on the exterior face of the other panel.

16. The pillow covering of claim 15, further including:
pillow fill positioned in between the cover panels, wherein the cover panels being joined together along at least three of the opposed sides.

17. The pillow covering of claim 14, wherein:
the length of the long side of the horizontal panels being at least about equal to one third the length of the long side of the cover panel.

18. The pillow covering of claim 17, wherein:
the long side of the horizontal panels being about equal to one half the length of the long side of the cover panel.

19. The pillow covering of claim 14, further including:
corner means for forming a corner where one of the cover panel short sides and an adjacent one of the cover panel long sides is joined with the opposed one of the cover panel short sides and the opposed one of the cover panel long sides.

20. The pillow covering of claim 19, wherein the pillow cover includes at least two corners.

21. The pillow covering of claim 14, further including said horizontal inserts, wherein said horizontal inserts are hot or cold packs.

22. A pillow, comprising:
a pillow having two long sides joined at four points with two short sides, the four points defining a rectangle, the pillow having opposing front and back panels which enclose pillow fill therebetween, the front and back panels each having an interior and exterior panel face, and the interior and exterior panel faces each having a panel face center region having a width, panel face top and bottom regions located on opposite sides of each panel face, and panel face first and second side regions located on opposite sides of each panel face and perpendicular to the panel face top and bottom regions, the panel face top regions being adjacent one of the long sides of the pillow and the panel face bottom regions being adjacent the other long side of the pillow;
a top pocket means for substantially enclosing a top pocket insert, said top pocket means secured to one of the exterior panel face top regions of said pillow; and
a bottom pocket means for substantially enclosing a bottom pocket insert, said bottom pocket means secured to one of the exterior panel face bottom regions of said pillow, said top pocket means and said bottom pocket means being spaced apart a distance equal to the width of said panel face center region to expose said panel face center region.

23. The pillow of claim 22, wherein:
said top pocket means is removable; and
said bottom pocket means is removable.

24. The pillow of claim 22, wherein:
said top pocket means comprises a substantially rectangular top rectangular panel having two long sides and two short sides;
said bottom pocket means comprises a bottom rectangular panel, substantially identical to said top rectangular panel; and
said top rectangular panel being positioned such that one of its long sides is substantially parallel to one of the long sides of said bottom rectangular panel.

25. The pillow of claim 24, wherein:

the length of the long sides of said top and bottom rectangular panels is at least about equal to one third the length of the longest dimension across said cover element.

26. The pillow of claim 25, wherein:
the length of the long sides of said top and bottom rectangular panels is about equal to one half the length of the longest dimension across said cover element.

27. The pillow of claim 24, further comprising:
a top pocket insert enclosed within said top pocket means; and
a bottom pocket insert enclosed within said bottom pocket means.

28. The pillow of claim 27, wherein:
said top pocket insert comprises a hot/cold pack; and
said bottom pocket insert comprises a hot/cold pack.

29. The pillow of claim 24, further comprising:
a center pocket means for substantially enclosing a center pocket insert, said center pocket means secured to one of the exterior panel face center regions of said pillow.

30. The pillow of claim 29, wherein:
said top pocket means is removable;
said bottom pocket means is removable; and
said center pocket means is removable.

31. The pillow of claim 29, wherein:
said center pocket means comprises a substantially rectangular center rectangular panel; and
said center rectangular panel positioned such that one of its sides is substantially parallel to the long sides of said top and bottom rectangular panels.

32. A pillow cover for covering a pillow, comprising:
a cover element having opposing front and back panels for substantially enclosing the pillow therebetween, the front and back panels each having an interior and exterior panel face, and the interior and exterior panel faces each having a panel face center region, panel face top and bottom regions located on opposite sides of each panel face, and panel face first and second side regions located on opposite sides of each panel face and perpendicular to the panel face top and bottom regions;
a first side pocket means for substantially enclosing a first side pocket insert, said first side pocket means secured to one of the panel face first side regions of said cover element;
a second side pocket means for substantially enclosing a second side pocket insert, said second side pocket means secured to one of the panel face second side regions of said cover element; and
a center pocket means for substantially enclosing a center pocket insert, said center pocket means secured to one of the panel face center regions of said cover element;
wherein said first side pocket means is removable, said second side pocket means is removable, and said center pocket means is removable.

33. A pillow cover for covering a pillow, comprising:
a cover element having opposing front and back panels for substantially enclosing the pillow therebetween, the front and back panels each having an interior and exterior panel face, and the interior and exterior panel faces each having a panel face center region, panel face top and bottom regions located on opposite sides of each panel face, and panel face first and second side regions located on opposite sides of each panel face and perpendicular to the panel face top and bottom regions;
a first side pocket means for substantially enclosing a first side pocket insert, said first side pocket means secured to one of the panel face first side regions of said cover element;
a second side pocket means for substantially enclosing a second side pocket insert, said second side pocket means secured to one of the panel face second side regions of said cover element;
a center pocket means for substantially enclosing a center pocket insert, said center pocket means secured to one of the panel face center regions of said cover element;
wherein said first side pocket means comprises a substantially rectangular first side rectangular panel having two long sides and two short sides;
wherein said second side pocket means comprises a second side rectangular panel, substantially identical to said first side rectangular panel;
wherein said first side rectangular panel is positioned such that one of its long sides is substantially parallel to one of the long sides of said second side rectangular panel;
wherein said center pocket means comprises a substantially rectangular center rectangular panel having two sides with lengths shorter then the long sides of said first and second side rectangular panels; and
wherein said center rectangular panel is positioned such that its short sides are substantially parallel to the long sides of said first and second side rectangular panels.

34. The pillow cover of claim 33, wherein:
the length of the short sides of said first and second side rectangular panels is at least about equal to one quarter the length of the longest dimension across said cover element.

35. The pillow cover of claim 34, wherein:
the length of the short sides of said first and second side rectangular panels is about equal to one third the length of the longest dimension across said cover element.

36. The pillow cover of claim 33, wherein:
said first side pocket means is secured to one of the exterior panel face first side regions;
said second side pocket means is secured to one of the exterior panel face second side regions; and
said center pocket means is secured to one of the exterior panel face center regions.

37. The pillow cover of claim 36, further comprising:
pillow fill positioned between the front and back panels of said cover element, said pillow fill being of ample quantity to come into contact with substantially all of the surface areas of the front and back panel interior faces of said cover element, and said pillow fill being of ample quantity to prevent the front panel interior face top, bottom, first side, and second side regions from coming into contact with the respective back panel interior face regions;
whereby, the pillow cover containing said pillow fill provides the same function as the pillow.

38. The pillow cover of claim 33, wherein:
said cover element comprises a rectangular shape for covering a rectangularly shaped pillow having a rectilinear depression substantially in the center of the pillow;
said cover element comprises boxed off corner means for giving said cover element more depth, whereby the rectangularly shaped pillow is not compressed when it is housed inside said cover element; and
said center pocket means having a perimeter at least as large as the perimeter of the rectilinear depression of the rectangularly shaped pillow.

* * * * *